United States Patent [19]

Turturro

[11] Patent Number: 5,895,361

[45] Date of Patent: Apr. 20, 1999

[54] ESOPHAGEAL BIOPSY JAW ASSEMBLY AND ENDOSCOPIC INSTRUMENT INCORPORATING THE SAME

[75] Inventor: Vincent Turturro, Miramar, Fla.

[73] Assignee: Symbiosis Corporation, Miami, Fla.

[21] Appl. No.: 08/801,067

[22] Filed: Feb. 14, 1997

[51] Int. Cl.[6] .................................................. A61B 10/00
[52] U.S. Cl. .......................... 600/562; 600/564; 30/124
[58] Field of Search .................................. 600/564, 565, 600/550, 570, 571, 33, 562; 606/110, 127, 205–207, 167, 170, 174; 30/115, 117, 124, 134

[56] References Cited

U.S. PATENT DOCUMENTS

| | | |
|---|---|---|
| 3,001,522 | 9/1961 | Silverman . |
| 3,175,554 | 3/1965 | Stewart . |
| 3,404,677 | 10/1968 | Springer ................................ 606/205 |
| 3,989,033 | 11/1976 | Halpern et al. . |
| 3,989,049 | 11/1976 | Yoon . |
| 4,200,111 | 4/1980 | Harris . |
| 4,393,872 | 7/1983 | Reznick . |
| 4,522,206 | 6/1985 | Whipple et al. . |
| 4,651,752 | 3/1987 | Fuerst . |
| 4,651,753 | 3/1987 | Lifton . |
| 4,721,116 | 1/1988 | Schintgen et al. . |
| 4,733,662 | 3/1988 | DeSatnick . |
| 4,763,669 | 8/1988 | Jaeger . |
| 4,880,015 | 11/1989 | Nierman . |
| 4,881,550 | 11/1989 | Kothe . |
| 4,887,612 | 12/1989 | Esser et al. . |
| 4,896,678 | 1/1990 | Ogawa . |
| 4,953,559 | 9/1990 | Salerno . |
| 4,976,723 | 12/1990 | Schad ................................ 606/170 |
| 5,052,402 | 10/1991 | Bencini et al. . |
| 5,082,000 | 1/1992 | Picha et al. . |
| 5,171,255 | 12/1992 | Rydell . |
| 5,172,700 | 12/1992 | Bencini et al. . |
| 5,217,458 | 6/1993 | Parins . |
| 5,219,357 | 6/1993 | Honkanen et al. . |
| 5,224,931 | 7/1993 | Kumar . |
| 5,228,451 | 7/1993 | Bales et al. . |
| 5,238,002 | 8/1993 | Devlin et al. . |
| 5,254,130 | 10/1993 | Poncet et al. . |
| 5,258,005 | 11/1993 | Christian . |
| 5,275,608 | 1/1994 | Forman et al. . |
| 5,281,230 | 1/1994 | Heidmueller . |
| 5,312,391 | 5/1994 | Wilk . |
| 5,318,589 | 6/1994 | Lichtman . |
| 5,320,627 | 6/1994 | Sorensen et al. . |
| 5,330,502 | 7/1994 | Hassler et al. . |
| 5,334,198 | 8/1994 | Hart et al. . |

(List continued on next page.)

*Primary Examiner*—Richard J. Apley
*Assistant Examiner*—Justine R. Yu
*Attorney, Agent, or Firm*—Finnegan, Henderson, Farabow, Garrett & Dunner, L.L.P.

[57] ABSTRACT

An endoscopic bioptome includes a jaw assembly, a tubular member, and a control wire extending through the tubular member, where the distal end of the control wire and tubular member are both coupled to the jaw assembly, and the jaw assembly includes a pair of opposed end effectors having resilient arms and a pair of opposed resilient anchors oriented orthogonal of the end effectors. Preferably the end effectors and the anchors are formed from a super-elastic metal. The anchors are blunt-tipped and also include angled portions which urge the anchors away from each other. The end effectors include resilient arms having proximal angled portions and distal portions which terminate with end effector jaw cups. The proximal angled portions urge the jaw cups away from each other. The jaw cups each have a sharp cutting rim. Another embodiment of the jaw assembly include jaw cups having radially arranged teeth. The proximal portion of each arm and anchor is coupled to a threaded base member which is thread into the coil. The distal end of the wire is coupled to a sleeve. The proximal ends of the coil and wire are coupled to a manual actuation means for axially displacing one of the coil and wire relative to the other. Axial movement of the wire relative to the coil moves the sleeve over the arms of the end effectors and also over the anchors, thereby forcing the jaw cups together in a biting action and moving the anchors radially inward.

22 Claims, 11 Drawing Sheets

U.S. PATENT DOCUMENTS

| | | | |
|---|---|---|---|
| 5,352,237 | 10/1994 | Rodak et al. | 606/206 |
| 5,373,854 | 12/1994 | Kolozsi | 606/52 |
| 5,445,638 | 8/1995 | Rydell et al. | |
| 5,474,057 | 12/1995 | Makower et al. | |
| 5,474,571 | 12/1995 | Lang. | |
| 5,527,313 | 6/1996 | Scott et al. | |
| 5,538,008 | 7/1996 | Crowe. | |
| 5,542,432 | 8/1996 | Slater et al. | |
| 5,638,827 | 6/1997 | Palmer et al. | 606/205 |
| 5,665,096 | 9/1997 | Yoon | 606/139 |
| 5,665,100 | 9/1997 | Yoon | 606/170 |
| 5,709,697 | 1/1998 | Ratcliff et al. | 606/180 |

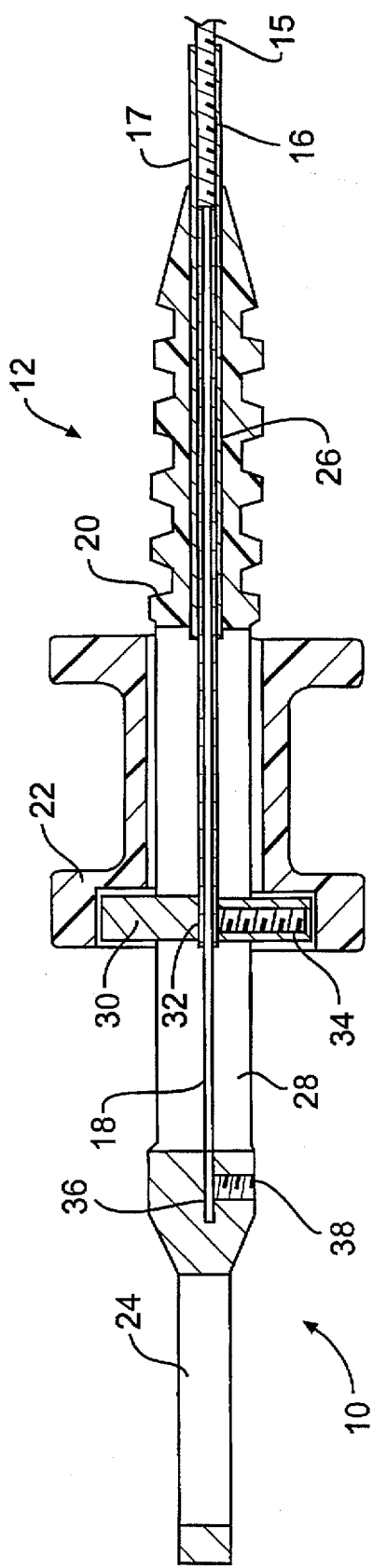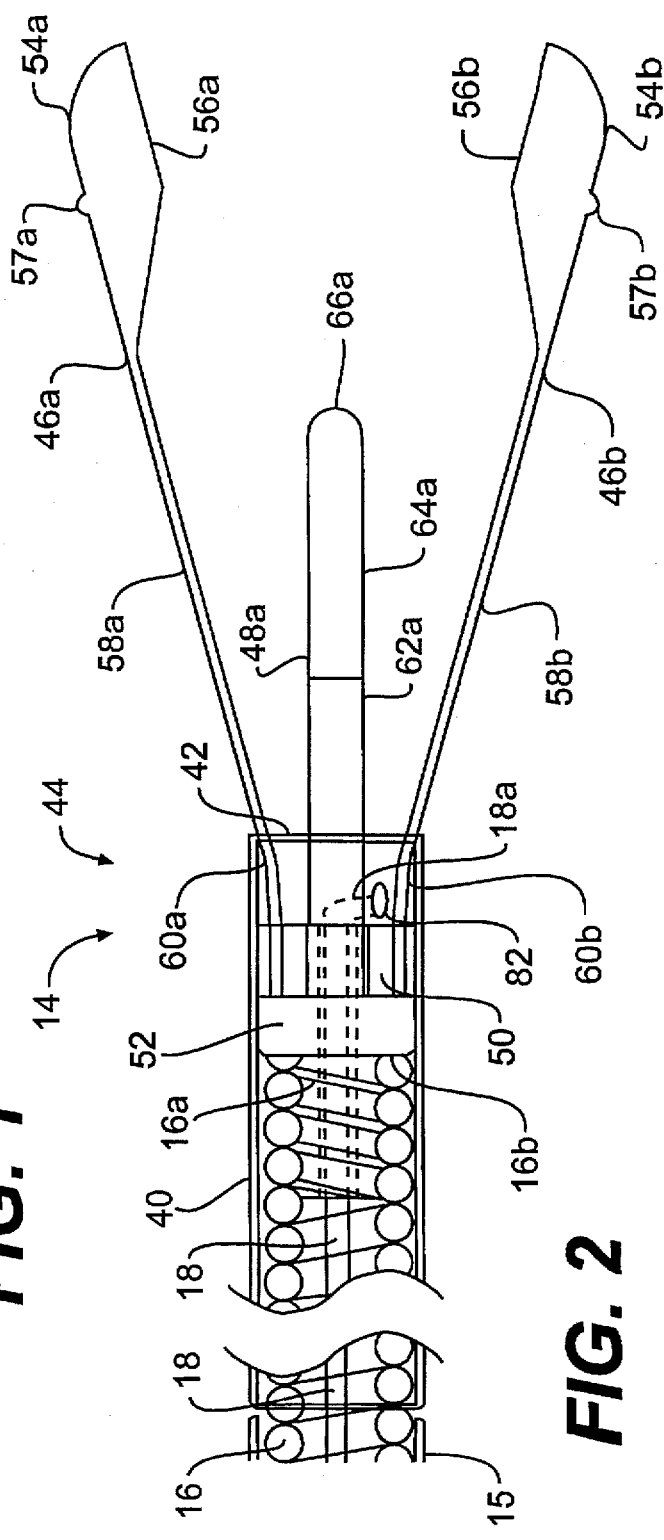
FIG. 1
FIG. 2

5,895,361

ESOPHAGEAL BIOPSY JAW ASSEMBLY AND ENDOSCOPIC INSTRUMENT INCORPORATING THE SAME

This application is related to U.S. Ser. No. 08/440,327, entitled "Jaw Assembly For An Endoscopic Instrument" now U.S. Pat. No. 5,645,075, U.S. Ser. No. 08/440,326, entitled "Super-Elastic Flexible Jaws Assembly For An Endoscopic Multiple Sample Bioptome" now U.S. Pat. No. 5,638,827, and U.S. Ser. No. 08/412,058, entitled "Endoscopic Multiple Sample Bioptome With Enhanced Biting Action", now U.S. Pat. No. 5,636,639. This application is also related to U.S. Pat. No. 5,542,432, entitled "Endoscopic Multiple Sample Bioptome." The above referenced U.S. Patents and applications are hereby incorporated by reference herein in their entireties.

BACKGROUND OF THE INVENTION

1. Field of the Invention

This invention relates broadly to endoscopic surgical instruments. More particularly, this invention relates to jaw assemblies for endoscopic biopsy forceps instruments.

2. State of the Art

Endoscopic biopsy procedures are typically performed with an endoscope and an endoscopic biopsy forceps device (bioptome). The endoscope is a long flexible tube carrying fiber optics and having a narrow lumen through which the bioptome is inserted. The bioptome typically includes a long flexible coil having a pair of opposed jaws at the distal end and manual actuation means at the proximal end. Manipulation of the actuation means opens and closes the jaws. During a biopsy tissue sampling operation, the surgeon guides the endoscope to the biopsy site while viewing the biopsy site through the fiber optics of the endoscope. The bioptome is inserted through the narrow lumen of the endoscope until the opposed jaws arrive at the biopsy site, which is typically a relatively large body cavity, e.g., the stomach or large intestine. While viewing the biopsy site through the fiber optics of the endoscope, the surgeon directs endoscope toward the sample tissue site, moves the jaws head on to the tissue site, and positions the jaws around the sample tissue. The surgeon manipulates the actuation means so that the jaws close around the tissue and a sample of the tissue is then cut and/or torn away from the biopsy site while it is trapped between the jaws of the bioptome. Keeping the jaws closed, the surgeon withdraws the bioptome from the endoscope and then opens the jaws to collect the biopsy tissue sample.

Not all biopsy sites are large enough to enable the surgeon to adequately direct the endoscope and the jaws in a desired manner to a sample site. For example, the esophagus is relatively narrow, and it is difficult to turn and orient the endoscope within the esophagus to thereby aim a jaw assembly exiting a lumen of the endoscope toward the desired sample site; the sample site being typically located lateral of the distal end of the endoscope. Thus, in esophageal applications, it is common for the jaws to exit the endoscope and continue through the esophagus and fail to properly engage the wall of the esophagus for biopsy sampling.

In addition, an esophageal biopsy tissue sampling procedure often requires the taking of several tissue samples either from the same or from different biopsy sites. Unfortunately, most bioptomes are limited to taking a single tissue sample, after which the device must be withdrawn from the endoscope and the tissue collected before the device can be used again to take a second tissue sample. The single-sample limitation of most bioptomes is due to the limited space between the biopsy forceps jaws.

Several attempts have been made to provide an instrument which will allow the taking of several tissue samples before the instrument must be withdrawn and the samples collected. Problems in providing such an instrument include the extremely small size required by the narrow lumen of the endoscope and the fact that the instrument must be flexible in order to be inserted through the lumen of the endoscope. Thus, several known multiple sample biopsy instruments are precluded from use with an endoscope because of their size and rigidity. These include the "punch and suction type" instruments disclosed in U.S. Pat. No. 3,989,033 to Halpern et al. and No. 4,522,206 to Whipple et al.

Related efforts have been made to provide a multiple sampling ability to an instrument which must traverse the narrow lumen of an endoscope. These efforts have concentrated on providing a cylindrical storage space at the distal end of the instrument wherein several tissue samples can be accumulated before the instrument is withdrawn from the endoscope. U.S. Pat. No. 4,651,753 to Lifton, for example, discloses a rigid cylindrical member attached to the distal end of a first flexible tube and having a lateral opening. A second flexible tube is coupled to a knife blade for moving the knife blade relative to the lateral opening in the cylindrical member. A tissue sample is taken by bringing the lateral opening of the cylindrical member upon the biopsy site, applying vacuum with the syringe to draw tissue into the lateral opening, and pushing the second flexible tube forward to move the knife blade across the lateral opening. A tissue sample is thereby cut and trapped inside the cylindrical knife within the cylindrical member. However, the device of the Lifton patent suffers from several serious drawbacks. First, the Lifton device is designed to sample laterally of the device by using a syringe to help draw the tissue into the lateral opening, yet the nature of esophageal tissue does not lend itself to being drawn by suction, as the tissue is fairly tough. Second, the Lifton patent requires substantial effort on the part of the surgeon and an assistant and much of this effort is involved in pushing tubes, an action which is counter-intuitive to classical biopsy sampling. The preferred mode of operation of virtually all endoscopic tools is that a gripping action at the distal end of the instrument is effected by a similar action at the proximal end of the instrument. Classical biopsy forceps jaws are closed by squeezing a manual actuation member in a syringe-like manner.

A more convenient endoscopic multiple sample biopsy device is disclosed in U.S. Pat. No. 5,171,255 to Rydell. Rydell provides a flexible endoscopic instrument with a knife-sharp cutting cylindrical sleeve at its distal end. A coaxial anvil is coupled to a pull wire and is actuated in the same manner as conventional biopsy forceps. Ostensibly, when the anvil is drawn into the cylinder, tissue located between the anvil and the cylinder is cut and pushed into a storage space within the cylinder. Several samples may be taken and held in the storage space before the device is withdrawn from the endoscope. While the device of Rydell is purportedly effective in providing a multiple sample tool, it is limited to the lateral cutting of relatively loose tissue, unlike the tough tissue found in the esophagus.

Generally, tough tissue like that found in the esophagus is more effectively sampled with a forceps having jaws, as disclosed in co-owned U.S. Pat. No. 5,542,432 to Slater et al. Slater et al. discloses an endoscopic multiple sample biopsy forceps having a jaw assembly which includes a pair of opposed toothed jaw cups each of which is coupled by a resilient arm to a threaded base member. The threaded base member of the jaw assembly is mounted inside a cylindrical sleeve and axial movement of one of the jaw assembly and cylindrical sleeve relative to the other draws the arms of the jaws into the cylindrical sleeve or moves the cylindrical sleeve over the arms of the jaws to bring the jaw cups together in a biting action. The arms of the jaws effectively form a storage chamber which extends proximally from the lower jaw cup and prevents accumulated biopsy samples from being squeezed laterally out from between the jaws during repeated opening and closing of the jaws and the lower jaw cup enhances movement of the biopsy samples into the storage chamber.

Co-owned U.S. Ser. No. 08/440,327 to Palmer et al. improves on this concept by providing super-elastic jaw arms and jaw cups to the jaws assembly. Super-elastic jaw arms are extremely flexible and repeatedly return to desired positions without fracturing or deforming. In addition, super-elastic jaw arms do not significantly plastically deform, even after repeatedly being opened and forced closed. This instrument excels at taking samples of tissue located in front of the jaw assembly.

However, as discussed above, the narrow space of the esophagus hinders the distal portion of the endoscope from adequately aligning the biopsy instrument in a head-on direction.

SUMMARY OF THE INVENTION

It is therefore an object of the invention to provide a jaw assembly for an endoscopic biopsy forceps which can be oriented to take tissue samples lateral of the distal end of an endoscope through which the endoscopic biopsy forceps is inserted.

It is another object of the invention to provide a jaw assembly for an endoscopic biopsy forceps which has anchors which assist in maneuvering the jaw assembly.

It is a further object of the invention to provide a jaw assembly for an endoscopic biopsy forceps where at least portions of the jaw assembly are made out of a super-elastic metal.

In accord with these objects which will be discussed in detail below, an endoscopic bioptome is provided with a jaw assembly, a tubular member, and a control wire extending through the tubular member, where the distal end of the wire and tubular member are both coupled to the jaw assembly, and the jaw assembly includes a pair of opposed resilient anchors and a pair of opposed end effectors having resilient arms. Preferably the arms and the anchors are formed from a super-elastic metal alloy. The proximal ends of the resilient arms include angled portions, while the distal ends terminate with end effector jaw cups having sharp cutting rims, which are also preferably formed from a super-elastic metal. The resilient arms urge the jaw cups away from each other. The anchors are blunt-tipped and also include angled portions, which urge the anchors away from each other. Another embodiment of the jaw assembly includes jaw cups having radially arranged teeth.

According to preferred aspects of the invention, the tubular member is a flexible coil, and the proximal portion of each arm and anchor is mounted inside the distal end of the coil by means of a threaded base member thread into the coil. The distal end of the wire is coupled to a cylindrical sleeve. The proximal ends of the coil and wire are coupled to a manual actuation means for axially displacing one of the coil and wire relative to the other. Axial movement of the wire relative to the coil moves the cylindrical sleeve over the arms of the end effectors and over the anchors, thereby forcing the jaw cups together in a biting action and moving the anchors radially inward, such that the jaw assembly is in a closed position.

It will be appreciated that the jaw assembly, in a closed position, is moved through an endoscope positioned in the esophagus and distal of the endoscope to the approximate site of which a tissue sample is desired. The cylindrical sleeve is then drawn back from the jaw assembly, such that the jaw assembly is in an open position. A distal movement of the jaw assembly causes one of the anchors to engage the tissue lining the esophagus. Continued distal movement of the endoscopic instrument causes the jaw assembly to deflect and rotate about the anchor and towards the tissue until the jaw cups contact the tissue. The actuation handle is then operated to move the cylindrical sleeve distally to close the jaw assembly in a biting action and to move the anchors radially inward. Other samples may then be taken in a similar manner or the biopsy instrument may be removed from the endoscope.

Additional objects and advantages of the invention will become apparent to those skilled in the art upon reference to the detailed description taken in conjunction with the provided figures.

BRIEF DESCRIPTION OF THE DRAWINGS

FIG. 1 is a broken side elevation in partial section of the proximal portion of the endoscopic instrument of the invention;

FIG. 2 is a broken side elevation in partial section of a distal assembly of the invention with the jaws and anchors in an open position;

DETAILED DESCRIPTION OF THE PREFERRED EMBODIMENTS

Figure 3:
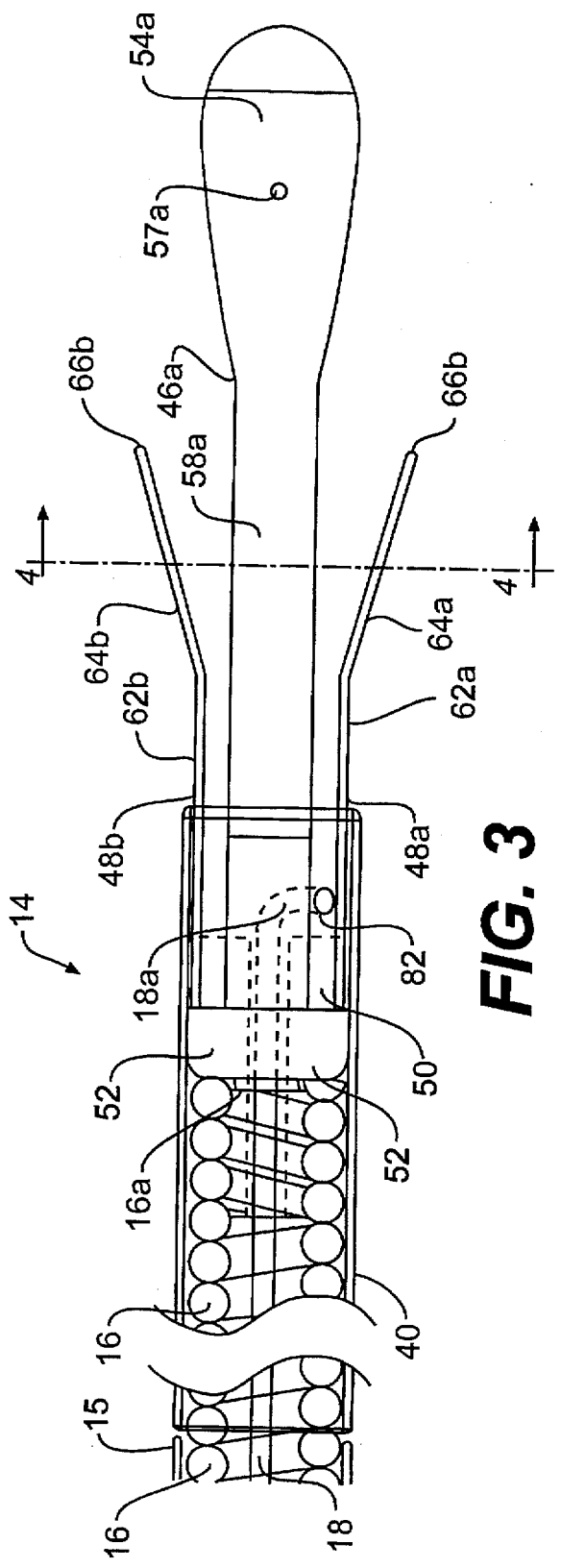
FIG. 3 is a broken top view in partial section of the distal assembly of FIG. 2.

Turning now to FIGS. 1 through 8, a first embodiment of the multiple sample bioptome 10 is shown and includes a proximal handle portion 12 and a distal assembly 14. A long flexible coil 16 and an axially displaceable control wire 18 which extends through the coil 16 couple the handle portion 12 to the distal assembly 14. The coil 16 is preferably covered with a PTFE, FEP or polyolefin sheath 15 along substantially all of its length and a strain relief sleeve 17 covering a portion of the coil which extends from the handle 12. The coil 16, by its nature is effectively internally threaded and can receive a threaded base member with mating threads, as discussed in further detail below, at its open distal end 16a which is preferably ground flat as shown at 16b. The proximal handle portion 12 includes a central shaft 20 and a displaceable spool 22. The proximal end of the shaft 20 is provided with a thumb ring 24 and a longitudinal bore 26 is provided at the distal end of the shaft 20. A longitudinal slot 28 extends from the proximal end of bore 26 to a point distal of the thumb ring 24. The displaceable spool 22 is provided with a cross member 30 which passes through the slot 28 in the central shaft 20. The cross member 30 is provided with a central through hole 32 and a radially engaging set screw 34. A short bore 36 and a radially engaging set screw 38 are provided in the shaft 20 distal of the thumb ring 24 with the bore 36 communicating with the longitudinal slot 28. The proximal end of the coil 16 extends into the central through hole 32 in the cross member 30 and is fixed there by the set screw 34. The proximal end of the control wire 18, passes through slot 28, is inserted into the short bore 36, and held there by the set screw 38. From the foregoing, those skilled in the art will appreciate that relative movement of the shaft 20 and spool 22 results in movement of the control wire 18 relative to the coil 16. Such action results in actuation of the end effectors and movement of the anchors as described in detail below.

Turning now to FIGS. 2 through 8, the distal assembly 14 includes a cylindrical sleeve 40 and a jaw assembly 44. The cylindrical sleeve has a distal edge 42, which, if desired may be knife sharp. The jaw assembly 44 includes a pair of end effectors 46a, 46b, a pair of side anchors 48a, 48b, a threaded base member 50, and a retaining sleeve 52.

Each end effector 46a, 46b includes a jaw cup 54a, 54b and a resilient, preferably narrow, arm 58a, 58b which extends proximally from the jaw cup 54a, 54b. Each jaw cup 54a, 54b preferably has a sharp cutting rim 56a, 56b (or radially arranged teeth as described in detail below) and a closing cam 57a, 57b, as described in previously incorporated co-owned Ser. No. 08/412,058. The narrow arm 58a, 58b includes a gently angled portion 60a, 60b, and a proximal portion 59a, 59b having a mounting hole 61a, 61b. Preferably, at least the gently angled portion 60a, 60b of the arms 58a, 58b, and more preferably the entire arms, are formed from super-elastic memory alloy such as Nitinol and are biased apart from each other, thereby urging the jaw cups 54a, 54b apart (as seen in FIG. 2). In addition, the arms 58a, 58b and the jaw cups 54a, 54b are preferably integral with each other, and the jaws cups are preferably formed from a super-elastic memory alloy. However, it should be appreciated that while it is preferable to form the entire arm 58a 58b and jaw cup 54a, 54b from a super-elastic memory alloy, the jaw cups may be made of any other material and attached to the resilient arms by any conventional and appropriate means. A more detailed description of the jaws cups is found in previously incorporated co-owned U.S. Ser. No. 08/440,326.

According to the preferred embodiment, each side anchor 48a, 48b includes a proximal arm 62a, 62b having a mounting hole 68a, 68b, an outwardly angled portion 64a, 64b and a blunt tip 66a, 66b. The side anchors are preferably formed of resilient material and more preferably are formed from a super-elastic memory alloy, e.g. Nitinol.

Figure 7:
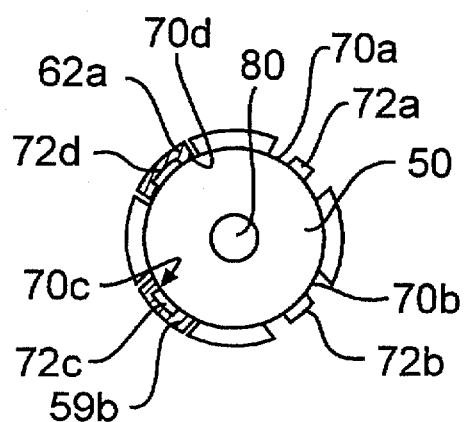
FIG. 7 is a cross section across line 7—7 in FIG. 6.
Figure 6:
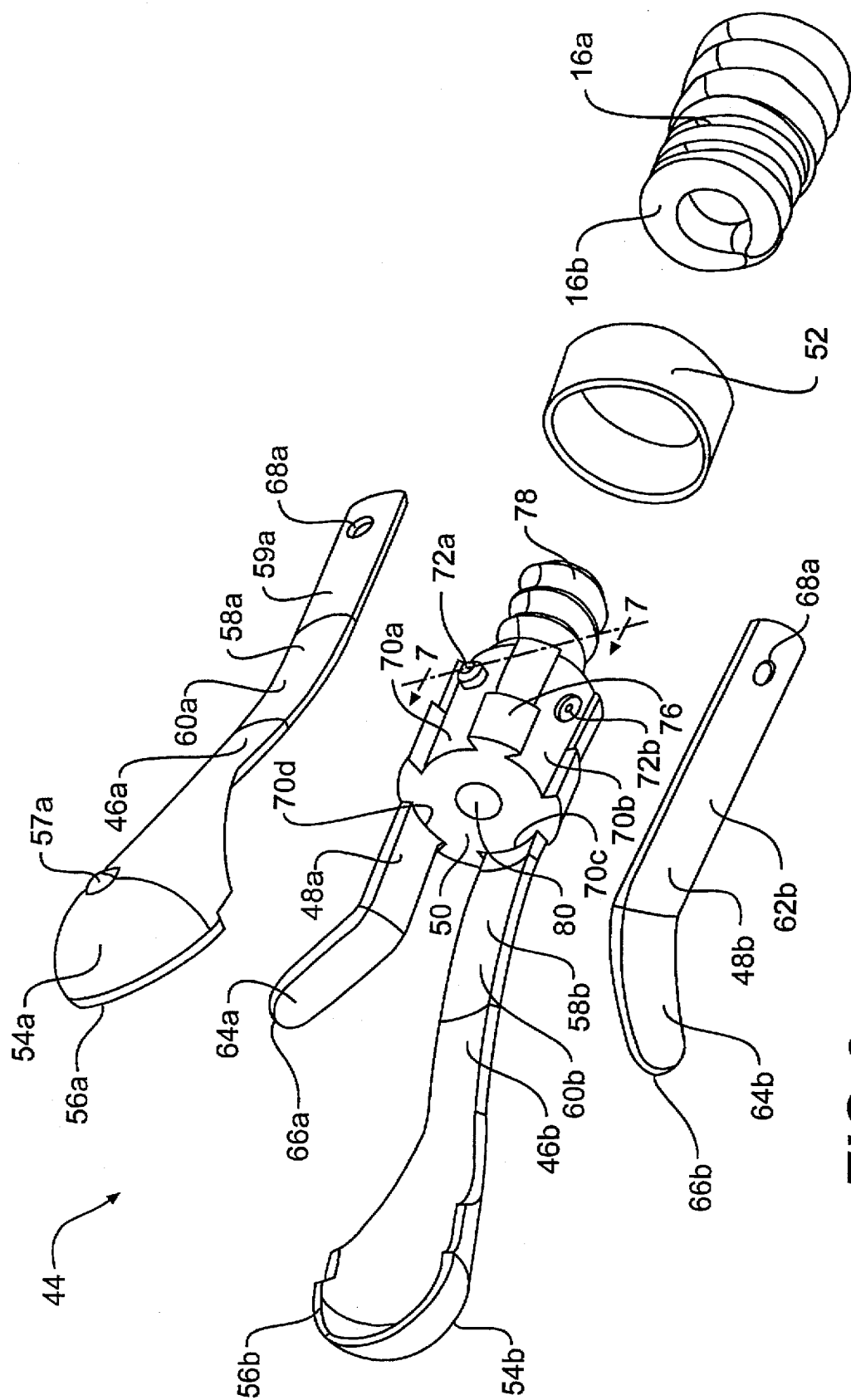
FIG. 6 is an exploded perspective view of the distal assembly of FIG. 2.
Figure 8:
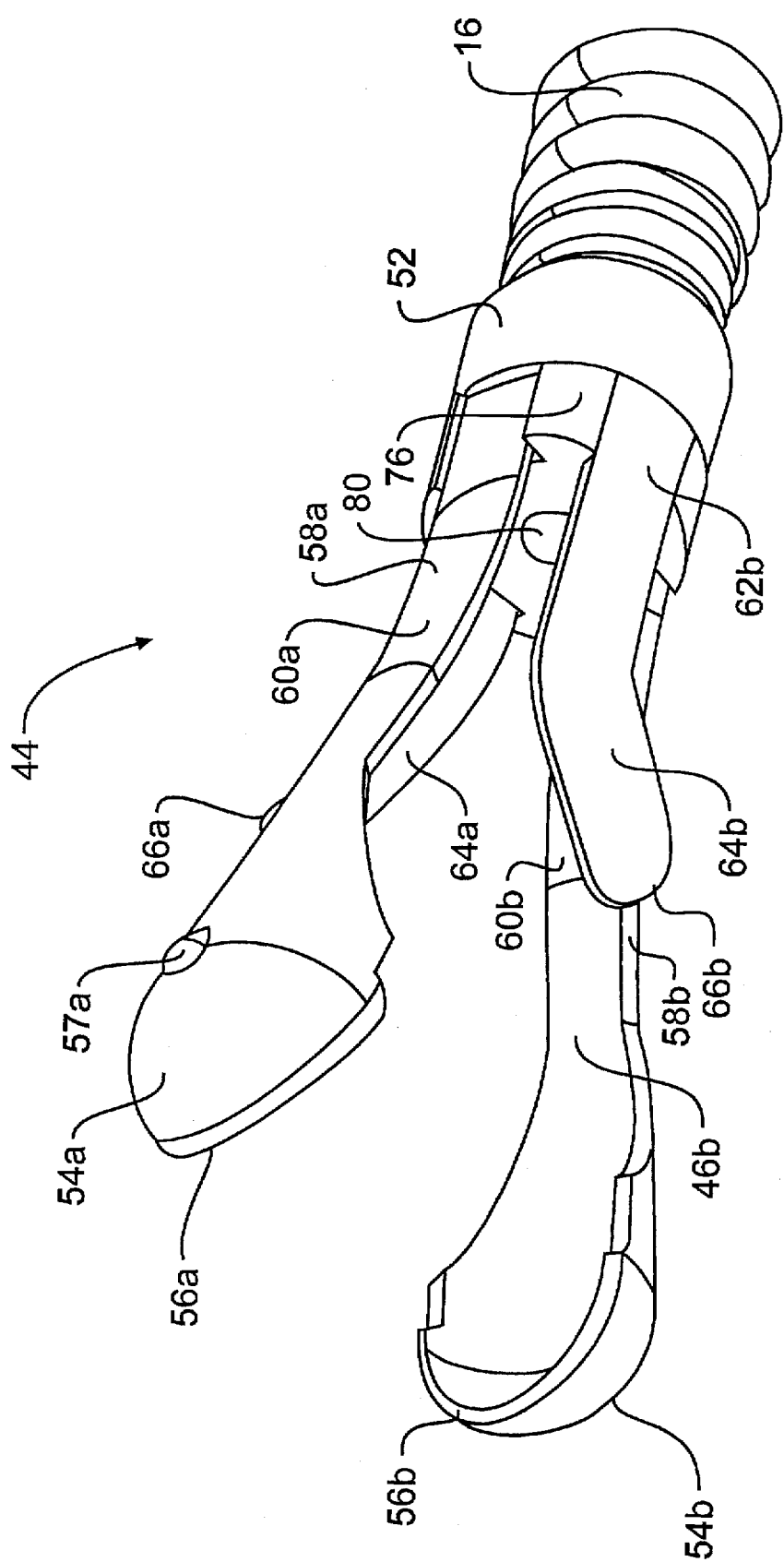
FIG. 8 is a perspective view of the distal assembly of FIG. 2.

In a presently preferred embodiment of the invention, as shown most clearly in FIGS. 6, 7, and 8, the threaded base member 50 has four lengthwise channels or grooves 70a–d, with the longitudinal center of each channel located at 90° intervals around the circumference of the threaded base member 50. Each channel 70a–d is provided with a boss 72a–d which protrudes slightly more than the thickness of each arm and anchor. As shown in FIGS. 6 and 8, the arms 46a, 46b and anchors 48a, 48b are coupled to the threaded base member 50 by respectively fitting the proximal portion 59a, 59b of each arm 58a, 58b and the proximal arm 62a, 62b of each anchor 48a, 48b into the channels 70a–d and respectively engaging the bosses 72a–d with the mounting holes 61a, 61b, 63a, 63b. The distal portion of the threaded base member includes a protrusion or lip 76. The proximal portion of the threaded base member 50 includes a male thread 78 adapted for threading the threaded base member into the distal end 16a of the coil 16. The threaded base member 50 also contains a throughbore 80 through which the control wire 18 can extend (see FIGS. 2 and 8). The retaining sleeve 52 extends over a central portion of the threaded base member and abuts against the lip 76, such that the arms 58a, 58b and the anchors 48a, 48b are secured to the threaded base member 50 (FIGS. 6 and 8).

Figure 5:
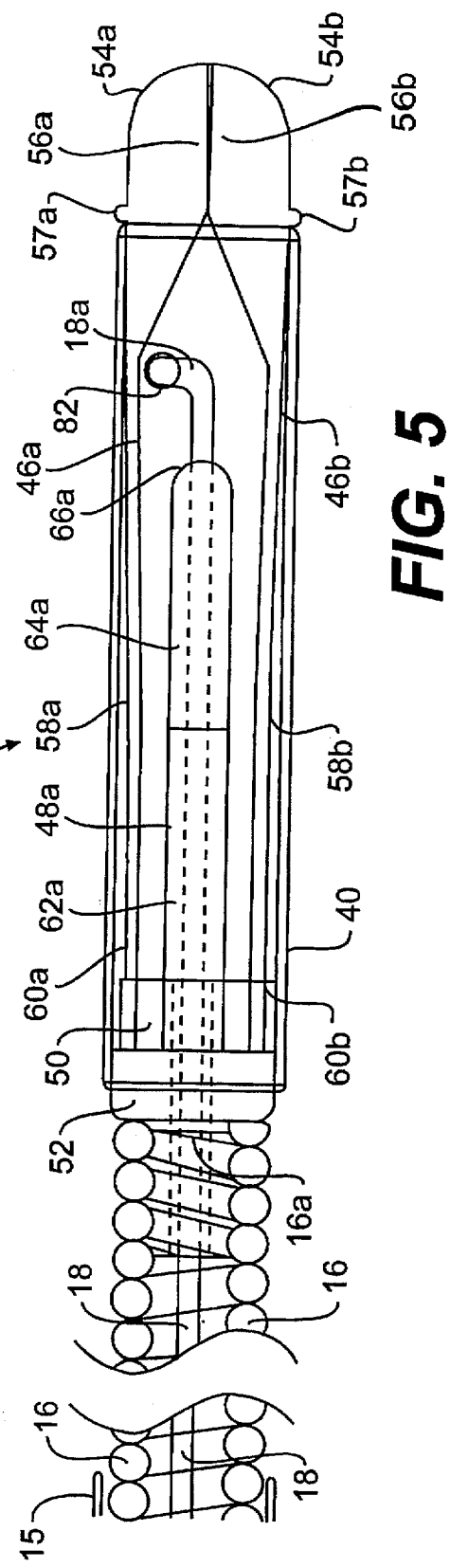
FIG. 5 is a broken side elevation in partial section of the distal assembly of FIG. 2 with the jaws and anchors in a closed position.
Figure 4:
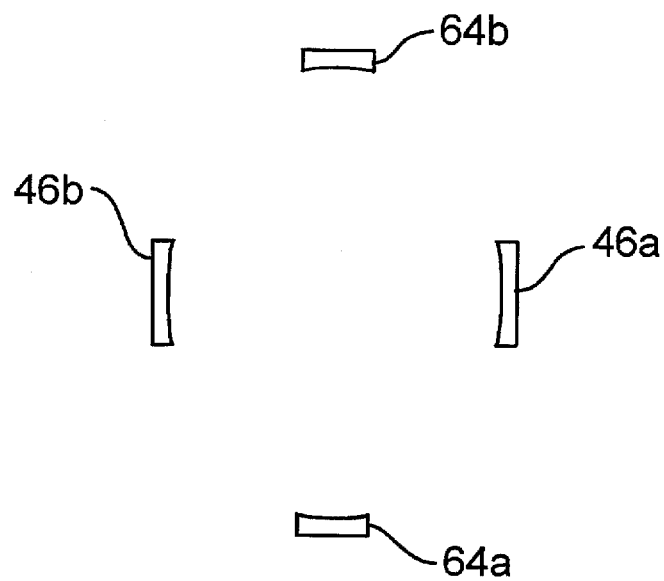
FIG. 4 is a cross section across line 4—4 in FIG. 3.

As seen in FIGS. 2, 3 and 5, the cylindrical sleeve 40 is coupled to the distal end of the control wire 18 by providing the sleeve 40 with a lateral hole 82 which receives a bent end 18a of the control wire 18. The bent end 18a of the control wire 18 is preferably welded to the hole 82 in the side of the sleeve 40. The cylindrical sleeve 40 is slidably mounted over the threaded base member 50 and the retaining sleeve 52 of the jaw assembly and is axially movable over the arms 46a, 46b and anchors 48a, 48b. When the cylindrical sleeve 40 extends distally over the jaw assembly 44, the cylindrical sleeve 40 bends the arms at the gently angled portions 60a, 60b and the anchors 48a, 48b at the outwardly angled portions 64a, 64b, thereby closing the jaw cups 54a, 54b and moving the blunt tips 66a (, 66b) of the anchors radially inward, as shown in FIG. 5. As the resilient arms 46a, 46b and anchors 48a, 48b are preferably made of super-elastic alloy, they will immediately return to their original open position (FIGS. 2 and 3) once the cylindrical sleeve 40 is retracted. Furthermore, even after repeatedly sliding the cylindrical sleeve 40 back and forth over the arms 58a, 58b and the anchors 48a, 48b, the jaw assembly 44 will maintain its original shape due to the properties of the super-elastic metal, as described in detail in co-owned U.S. Ser. No. 08/440,326.

From the foregoing description and with reference to FIGS. 1 through 8, those skilled in the art will appreciate that when the spool 22 and the shaft 20 are axially displaced relative to each other, the cylindrical sleeve 40 is axially displaced relative to the end effectors 46a, 46b and the anchors 48a, 48b, from the positions shown in FIG. 2 to the positions shown in FIG. 5 and vice versa. When the spool 22 and shaft 20 are in the approximate position shown in FIG. 1, the cylindrical sleeve 40, the end effectors 46a, 46b, and the anchors 46a, 46b will be in the approximate position shown in FIG. 2; i.e., with the jaws open and the anchors angled outward. Thus, when the spool 22 is moved towards the thumb ring 24, or vice versa, the cylindrical sleeve 40, the end effectors 46a, 46b, and the anchors 48a, 48b will be brought into the approximate position shown in FIG. 5; i.e., with the jaws closed and the anchors bent inward. Moreover, it will also be appreciated that it is preferable to move the thumb ring 24 relative to the spool 22, rather than vice versa since that will move the cylindrical sleeve 40 relative to the end effectors 46a, 46b and the anchors 48a, 48b, rather than vice versa. This is desirable so that the end effectors are not moved away from a tissue sample while the jaws are being closed.

Figure 9:
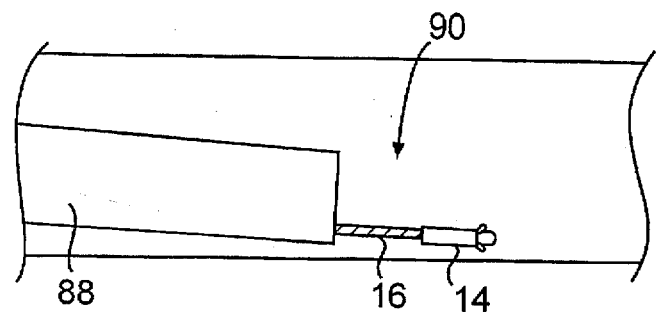
FIGS. 9–12 are broken side elevation views of the operation of the biopsy forceps instrument according to the invention.
Figure 10:
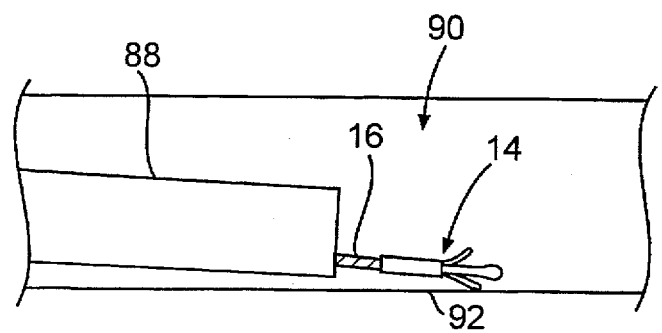
Figure 11:
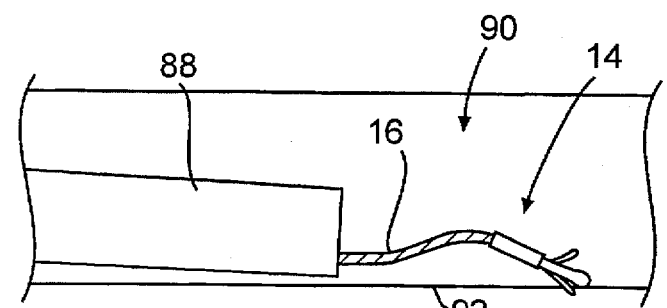
Figure 12:
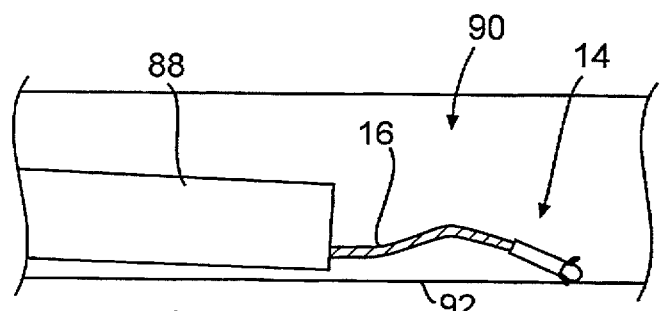
Figure 13:
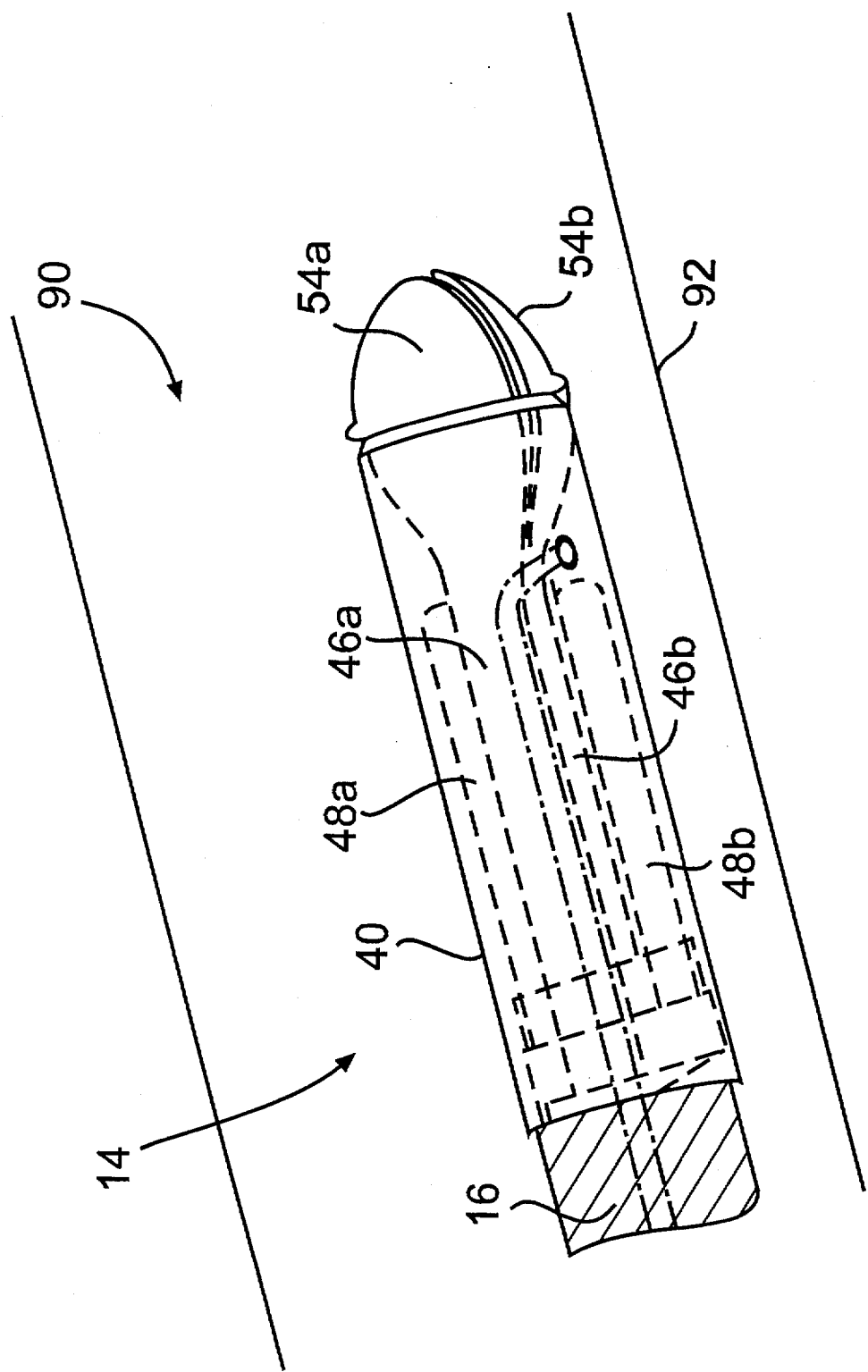
FIGS. 13–18 are perspective views of the operation of a biopsy forceps instrument according to the invention.
Figure 14:
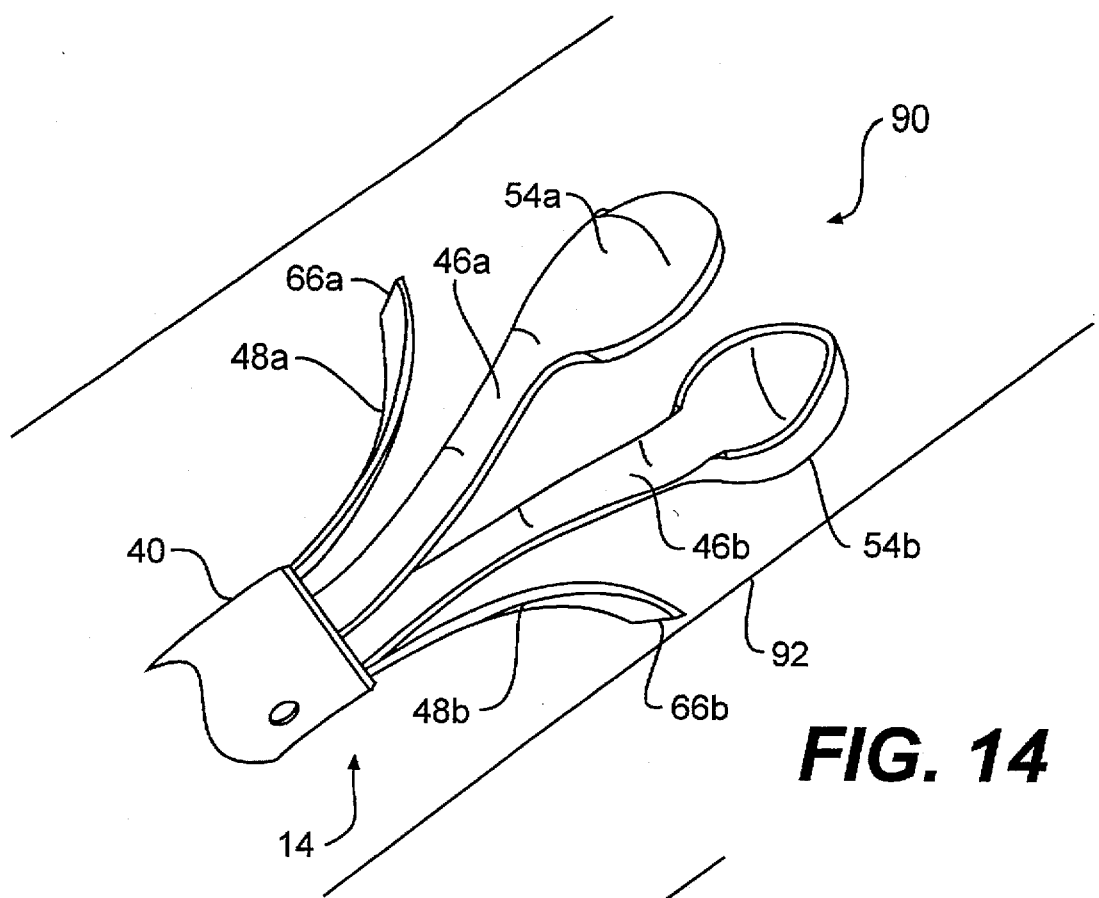
Figure 15:
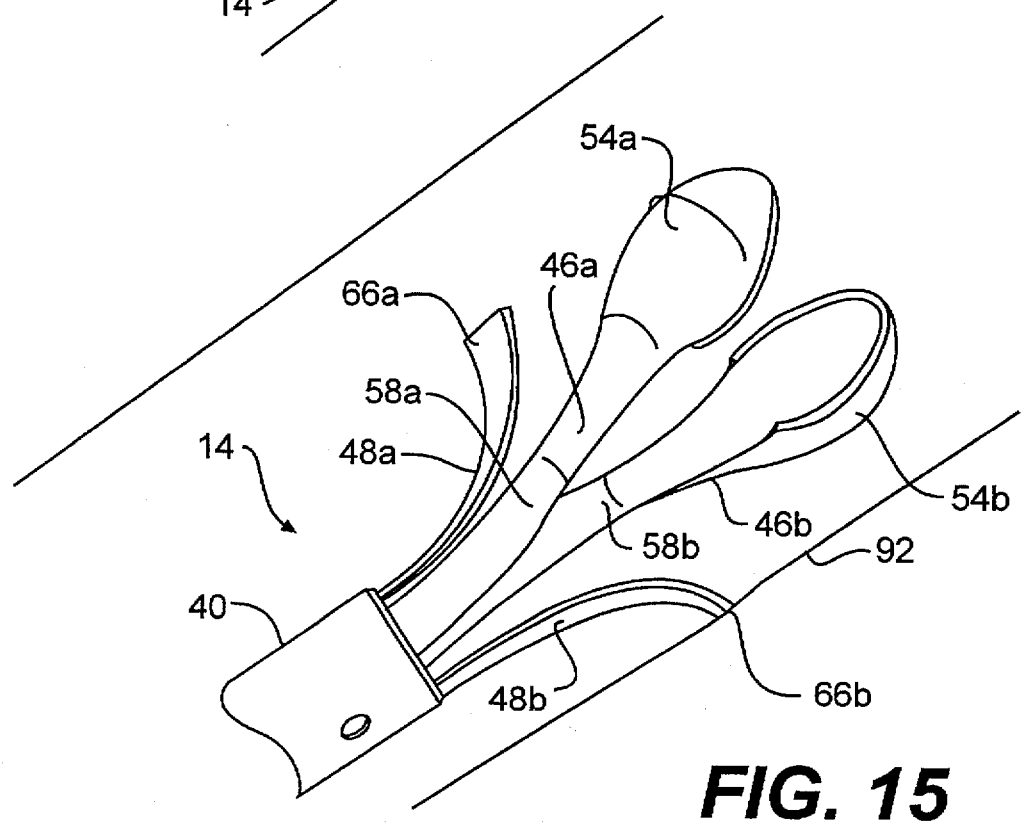
Figure 16:
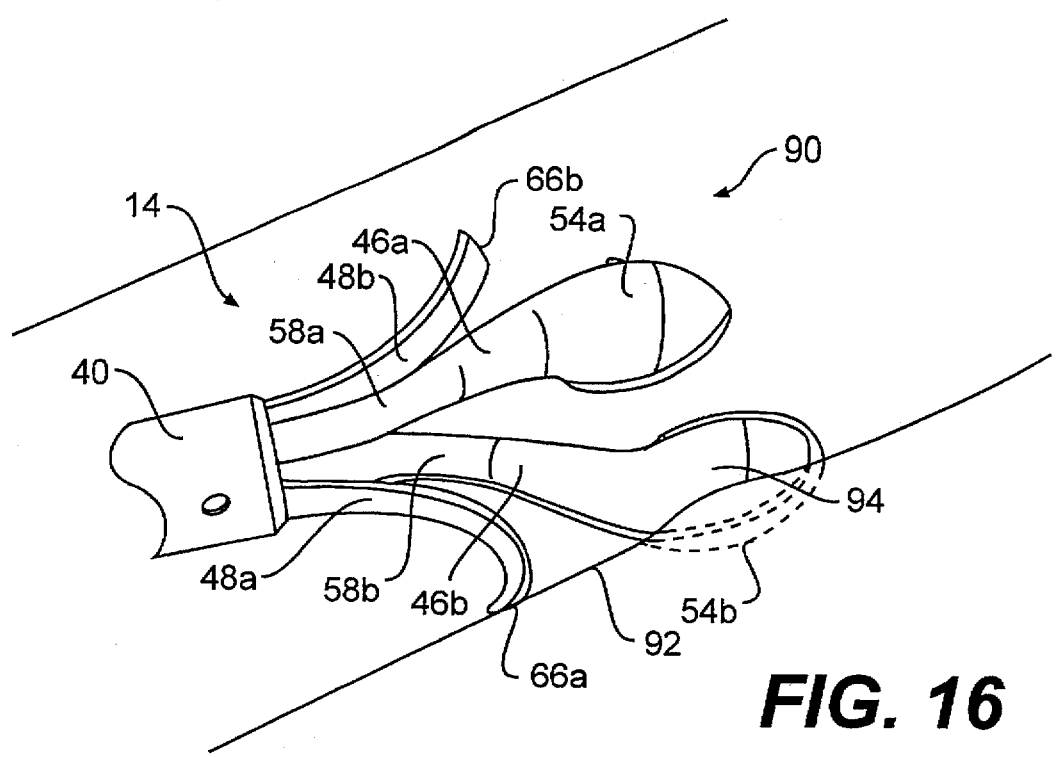
Figure 17:
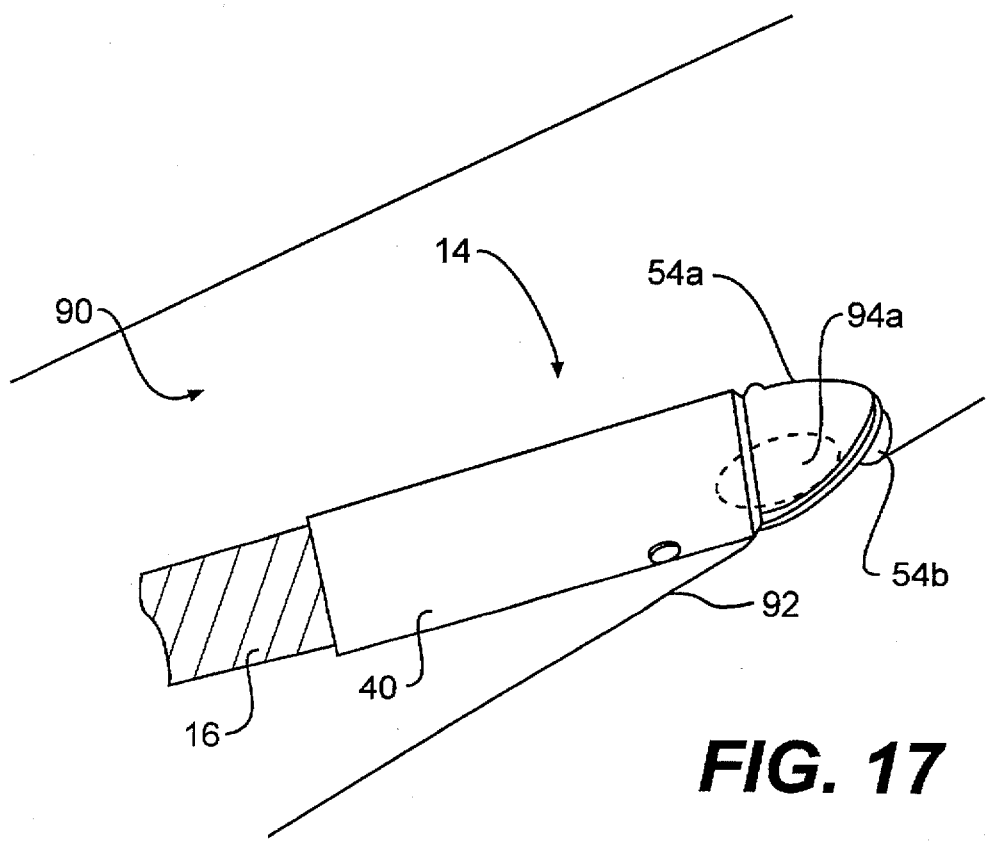

Turning now to FIGS. 9 through 18, the operation of the multiple sample bioptome of the invention is illustrated in sequence. As seen in FIGS. 9 and 13, first, the distal assembly 14, with the jaws and anchors in a closed position, is maneuvered through the endoscope 88 and into the esophagus 90. Second, the handle 12 (not shown) of the bioptome is operated as described above so that the cylindrical sleeve 40 is moved proximally over the arms 58a, 58b and anchors 48a, 48b of the jaw assembly 44 to the position approximately shown in FIGS. 10 and 14. Referring to FIG. 15, one of the outward bending anchors 48a engages the lining 92 of the esophagus 90. Moving the distal assembly 14 distally further into the esophagus 90 causes the distal assembly to deflect and rotate about the anchor engaged in the esophageal lining 92 and to be directed toward the tissue 94 to be sampled, as shown in FIGS. 11 and 16. The flexibility of the coil 16 permits that portion of the coil extending outside the endoscope 88 to be deflected with the distal assembly 14. It will be appreciated the super-elastic property of the anchor 48a promotes rotation of the distal assembly 14 about the anchor and helps to swing the distal assembly about the anchor and direct the jaw cups 54a, 54b toward the esophageal lining 92. It will also be appreciated that the blunt tip 66a and the elasticity of the anchor prevents the anchor from perforating or otherwise seriously damaging the esophageal lining. Referring to FIGS. 12 and 17, the proximal handle is next operated to move the cylindrical sleeve 40 distally over the arms and anchors of the jaw assembly. When the sleeve 40 is moved toward this position, the jaw cups 54a, 54b are brought close to each other and the sharp rims 56a, 56b of the jaw cups 54a, 54b engage the tissue 94 and bite into it, severing a sample 94a. It will also be appreciated that as the cylindrical sleeve moves distally over the end effectors 46a, 46b, the knife sharp distal edge 42 of the cylindrical sleeve 40 will cut off any loose tissue between the sample 94a in the end effectors and the esophageal lining 92. A first sample 94a of the tissue 94 is thereby trapped between the jaw cups 54a, 54b and severed from the lining 92.

Figure 18:
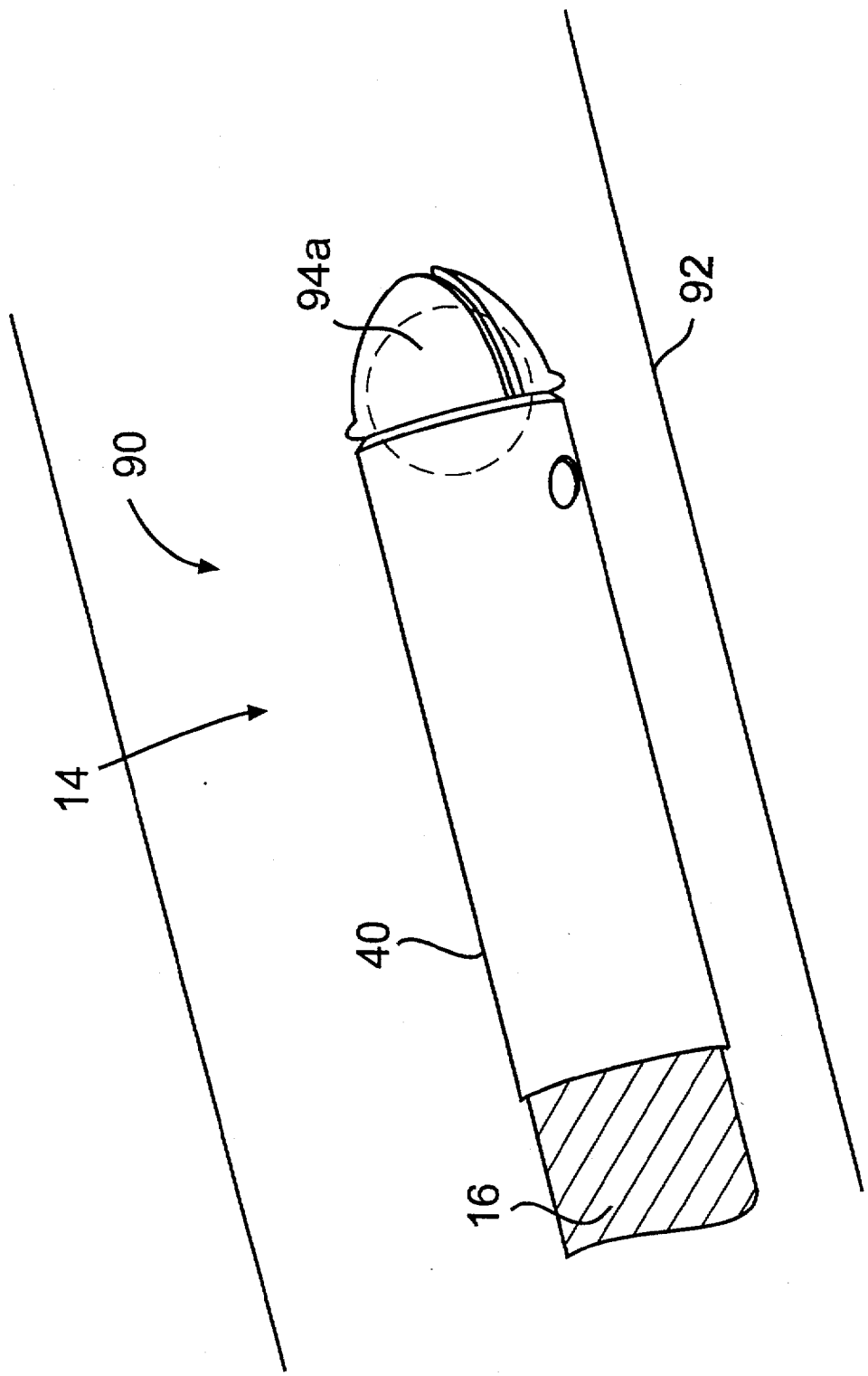

With the end effectors 46a, 46b in the position approximately shown in FIG. 18, the distal assembly 14 may be relocated to another tissue area for sampling in the similar manner. Those skilled in the art will appreciate that any consequent tissue sample will push the first sample 94a proximally away from the jaw cups 54a, 54b and into the space between the narrow arms 58a, 58b. Those skilled in the art will also appreciate that the tissue sample 94a is typically gummy and pliant and will stick to and move along one or both of the narrow arms 58a, 58b of the end effectors 46a, 46b. The samples will also stick to each other. The procedure described above may be repeated until the space between the arms 58a, 58b is filled with samples.

Figure 19:
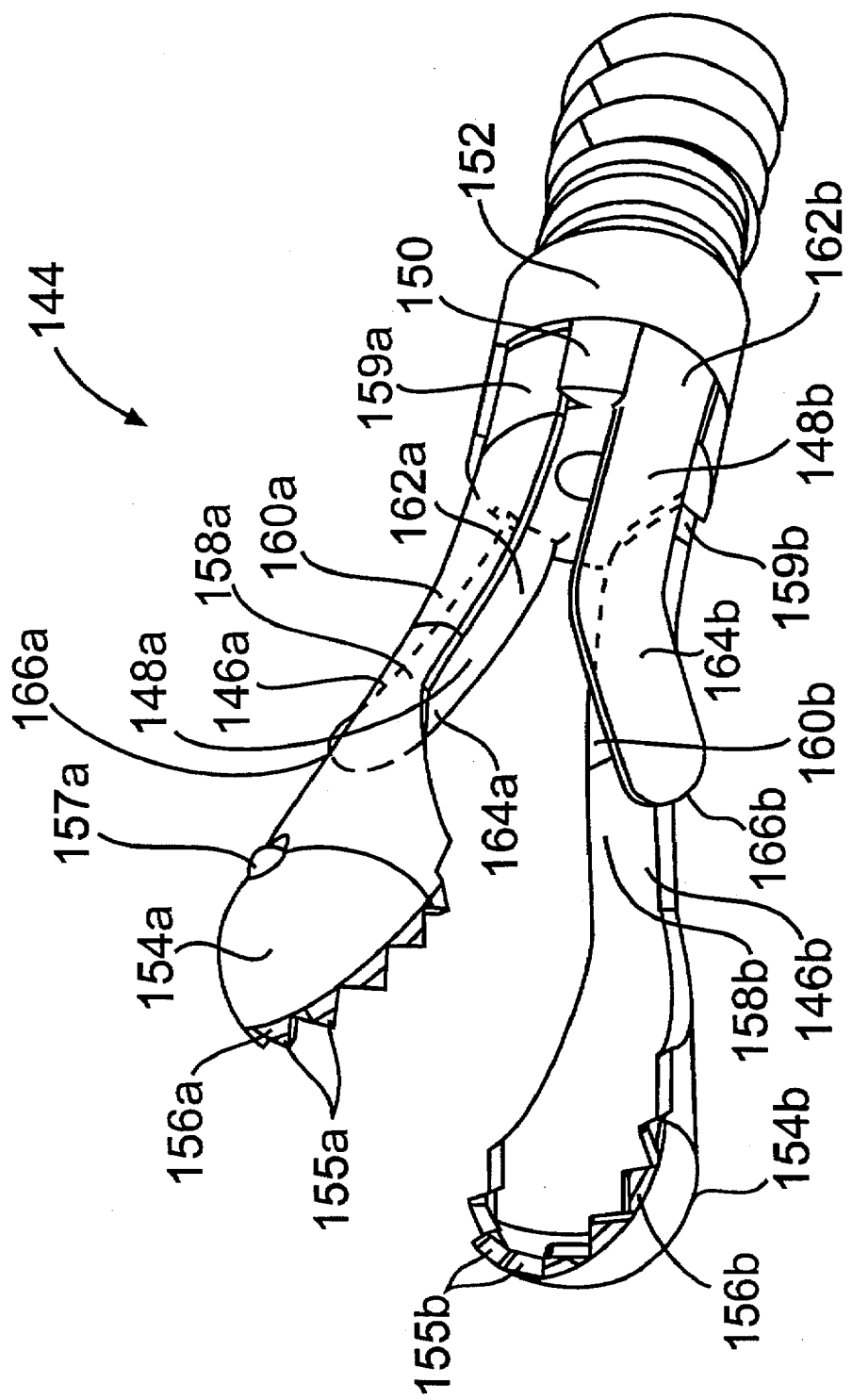
FIG. 19 is a perspective view of a distal assembly according to a second embodiment of the invention.

Turning to FIG. 19, a second embodiment of the jaw assembly 144 of the invention, substantially similar to the first embodiment (with like parts have numbers incremented by 100), is shown. The jaw assembly 144 includes a pair of end effectors 146a, 146b, a pair of anchors 148a, 148b, a threaded base member 150 and a retaining sleeve 152. The end effectors 146a, 146b includes a jaw cup 154a, 154b and a resilient, preferably narrow, arm 158a, 158b which extends proximally from the jaw cup 154a, 154b. Each jaw cup 154a, 154b preferably has a plurality of radially arranged sharp cutting teeth 155a, 155b around a rim 156a, 156b and a closing cam 157a, 157b, as described in previously incorporated co-owned Ser. No. 08/412,058. The narrow arm 158a, 158b includes a gently angled portion 160a, 160b, and a proximal portion 159a, 159b. The anchors 148a, 148b include a proximal arm 162a, 162b, an outwardly angled portion 164a, 164b and a blunt tip 166a, 166b. The end effectors 146a, 146b and anchors 148a, 148b and coupled to the threaded base member 150 by the retaining sleeve 152 in the same manner as in the first embodiment. It will be appreciated that the radially arranged teeth on the jaw cups may provide enhanced cutting action in some circumstances.

There have been described and illustrated herein several embodiments of an multiple sample bioptome for esophageal use. While particular embodiments of the invention have been described, it is not intended that the invention be limited thereto, as it is intended that the invention be as broad in scope as the art will allow and that the specification be read likewise. Thus, while a threaded base member has been disclosed for coupling the end effectors and the anchors together to the coil, it will be appreciated that other manners of coupling the end effectors and the anchors to the coil can be used as well, as disclosed in co-owned U.S. Ser. No. 08/440,326. In addition, while two anchors have been disclosed for deflecting the jaw assembly, it will be appreciated that a jaw assembly having only one anchor may also be used. Furthermore while the control wire has been shown to be coupled to the cylindrical sleeve by welding, it will be understood that other methods of coupling may be used. For example, and not by way of limitation, a Z-bend, as disclosed in U.S. Ser. No. 08/440,326, may be used. Moreover, it will be appreciated that the cylindrical sleeve may be coupled to the coil and the end effector assembly may be coupled to the control wire, as described in U.S. Pat. No. 5,542,432. It will therefore be appreciated by those skilled in the art that yet other modifications could be made to the provided invention without deviating from its spirit and scope as so claimed.

We claim:

1. An endoscopic biopsy forceps instrument, comprising:
   a) a tubular member having proximal and distal ends;
   b) a control member extending through the tubular member and having proximal and distal ends;
   c) a cylindrical member coupled to said distal end of one of said tubular member and said control member and having a longitudinal axis;
   d) a distal assembly having first and second end effectors and at least a first resilient anchor member, said first and second end effectors each having an arm biased away from said longitudinal axis and each having a distal jaw cup located at a distal end of said arm, and said first anchor member having a tip, wherein said anchor member engaging a tissue surface and directs said effectors into a desired position, said distal assembly coupled to the other of said tubular member and said control member not coupled to said cylindrical member; and
   e) actuation means coupled to said proximal ends of said tubular member and said control member for moving said control member relative to said tubular member and thereby moving said cylindrical member relative to said first and second end effectors and said first anchor member, such that said cylindrical member and said first and second end effectors and said first anchor member move relative to each other so as to cause said cylindrical member, in a first position, to extend over a portion of the first and second end effectors and said first anchor member so as to force said arms of said first and second end effectors and said tip of said first anchor member toward said longitudinal axis to assume a relatively closed position, and, in a second position, to permit said first and second end effectors to extend away from each other and to permit said first anchor member to bend outward from said longitudinal axis such that said first and second end effectors and said first anchor member assume a relatively open position.

2. An endoscopic biopsy forceps instrument according to claim 1, wherein:

said distal assembly includes a second anchor member having a proximal portion and a tip biased away from said longitudinal axis.

3. An endoscopic biopsy forceps instrument according to claim 2, wherein:

said tips of said first and second anchor members are substantially blunt.

4. An endoscopic biopsy forceps instrument according to claim 2, wherein:

said first and second anchor members are made of super-elastic metal alloy.

5. An endoscopic biopsy forceps instrument according to claim 2, wherein:

said distal assembly further includes a base member which couples said first and second end effectors and said first and second anchor members to said distal end of said tubular member, said base member being substantially cylindrical and including four longitudinal channels around a circumference of said base member, each of said longitudinal channels being offset by 90°, and wherein said first and second end effectors are each coupled in one of said channels and separated by 180° from each other, and said anchor members are each coupled in one of said channels and separated by 180° from each other.

6. An endoscopic biopsy forceps instrument according to claim 5, wherein:

said distal assembly further includes a retaining sleeve extending over said longitudinal channels of said base member.

7. An endoscopic biopsy forceps instrument according to claim 1, wherein:

said distal assembly further includes a base member for coupling said first and second end effectors and said first anchor member to said distal end of said tubular member, said base member including a threaded portion having threads dimensioned to engage said distal end of said tubular member.

8. An endoscopic biopsy forceps instrument according to claim 1, wherein:

said first and second jaw cups are each provided with a sharp cutting rim.

9. An endoscopic biopsy forceps instrument according to claim 1, wherein:

said first and second jaw cups are each provided with a plurality of radially arranged teeth.

10. The endoscopic biopsy forceps instrument of claim 1 wherein the tip of the resilient anchor member is biased away from the longitudinal axis of the cylindrical member.

11. An end effector assembly for an endoscopic instrument, the endoscopic instrument having a tubular member with proximal and distal ends, a control member with proximal and distal ends, closure means for closing said end effector assembly by extending over a portion of said end effector assembly, and an actuation means for causing relative movement of the closure means and said end effector assembly, said end effector assembly having a central longitudinal axis and comprising:

a) first and second end effectors each having an arm biased away from the longitudinal axis; and each having a jaw cup located at a distal end of said arm;

b) a first resilient anchor member having a proximal portion, and a tip, wherein said anchor member engaging a tissue surface and directs said effectors into a desired position; and c) coupling means for coupling said arms of said first and second end effectors and said proximal portion of said anchor member to the endoscopic instrument.

12. An end effector assembly according to claim 11, further comprising:

a second anchor member having a proximal portion, and a tip biased away from the longitudinal axis, said second anchor member coupled to said coupling means.

13. An end effector assembly according to claim 12, wherein:

said tips of said first and second anchor members are substantially blunt.

14. An end effector assembly according to claim 12, wherein:

said first and second anchor members are made of super-elastic metal alloy.

15. An end effector assembly according to claim 12, wherein:

said coupling means includes a base member for coupling said first and second end effectors and said first and second anchor members to the distal end of the tubular member, said base member being substantially cylindrical and including four longitudinal channels around the circumference of said base member, each of said longitudinal channels being offset by 90°, and wherein said first and second end effectors are each coupled in one of said channels and separated by 180° from each other, and said anchor members are each coupled in one of said channels and separated by 180° from each other.

16. An end effector assembly according to claim 15, wherein:

said base member includes a threaded portion having threads dimensioned to engage the distal portion of the tubular member.

17. An end effector assembly according to claim 15, wherein:

said coupling means further includes a retaining sleeve extending over said longitudinal channels of said base member.

18. An end effector assembly according to claim 11, wherein:

said coupling means includes a base member for coupling said first and second end effectors and said first anchor member to the distal end of the tubular member, said base member having a threaded portion dimensioned to engage the distal portion of the tubular member.

19. An end effector assembly according to claim 11, wherein:

said first and second jaw cups are each provided with a sharp cutting rim.

20. An end effector assembly according to claim 11, wherein:

said first and second jaw cups are each provided with a plurality of radially arranged teeth.

21. An end effector assembly according to claim 11, wherein:

said arms of said first and second end effectors are made of super-elastic metal alloy.

22. The end effector assembly according to claim 11 wherein the tip of the resilient anchor member is biased away from the longitudinal axis.

* * * * *